US00PP09670P

United States Patent [19]

Hill, Jr.

[11] Patent Number: Plant 9,670

[45] Date of Patent: Oct. 22, 1996

[54] GUZMANIA PLANT NAMED 487-1

[75] Inventor: Herbert H. Hill, Jr., Lithia, Fla.

[73] Assignee: Twyford International, Inc., Santa Paula, Calif.

[21] Appl. No.: 490,973

[22] Filed: Jun. 15, 1995

[51] Int. Cl.[6] ..... A01H 5/00

[52] U.S. Cl. ..... Plt./88.8

[58] Field of Search ..... Plt./88.8

*Primary Examiner*—James R. Feyrer

*Attorney, Agent, or Firm*—Foley & Lardner

[57] ABSTRACT

A new cultivar of Guzmania named 487-1 having miniature growth habit, and large, long-lasting, clean red-orange inflorescence with white tipped terminal bracts.

2 Drawing Sheets

The present invention relates to a new and distinct cultivar of Guzmania, genus within the family bromeliaceae, hereinafter referred to by the cultivar name 487-1. The new cultivar is a hybrid resulting from a cross identified below.

Guzmania comprise a genus of more than 100 species of herbaceous evergreen perennials suitable for cultivation in the home or under glass. Guzmania are predominantly epiphytic with a few terrestrial species and are native to the tropics. For the most part, the species vary in diameter from 7 or 8 inches to 3 or 4 feet and have rosettes of glossy, smooth edged leaves.

Floral bracts of Guzmania frequently have brilliant colors and may last for many months. The range of flower colors for Guzmania is generally from yellow through orange but may also include flame red and red-purple. White or yellow, tubular, three-petalled flowers may also appear on a stem or within the leaf rosette but are usually short lived.

Guzmania may be advantageously grown as pot plant for greenhouse or home use. Desirably the plants are shaded from direct sunlight, and during the spring to autumn period, the central vase-like part of the leaf rosette is normally filled with water.

Guzmania is native to tropical America. Leaves of Guzmania plants are usually formed as basal rosettes which are stiff and entire and in several vertical ranks. Guzmania have terminal spikes or panicles which are often bracted, with petals united in a tube about as long as the calyx.

Asexual propagation of Guzmania is frequently done through the use of tissue culture practices. Propagation can also be form off-shoots produced by the plant which may then be rooted. The resulting off-shoots are detached from the mother plant and may be grown in an appropriate soil or bark mixture. Many types are propagated relatively uniformly from seeds.

The new cultivar 487-1 is the product of a planned breeding program and was originated by the inventor Herbert H. Hill Jr., from a cross made during such program in Lithia, Fla. in 1983. The male or pollen parent was *Guzmania lingulata* minor×'Deanna'. The female, or seed parent was *Guzmania lingulata* minor×*lingulata* minor 'Magnifica'. The selection comprising the new variety was chosen from the progeny after commencement of flowering in 1985. Subsequent asexual propagation by off-shoots by the inventor in Goulds, Fla. has demonstrated that the combination of characteristics as herein disclosed for the new cultivar 487-1 are firmly fixed and are retained through successive generations of asexual reproduction.

The following combined characteristics distinguish Guzmania 487-1 from other cultivars of *G. lingulata* minor, including *G. lingulata* minor 'Empire' which is characterized by its miniature growth habit and red-orange inflorescence.

1. The inflorescence produced by 487-1 is large for the type, with bright red-orange bracts, and contrasting white tipped terminal bracts. The inflorescence remains in color longer than any other comparable commercial cultivar tested.

2. The plant produces more leaves than comparable varieties, before flowering.

3. The leaves of 487-1 are medium green suffused with purple at the base, and are held upright. The plant seldom develops leaf-tip browning.

4. Flowers are present in the terminal part of the spike. The tips of the flowers emerge only slightly from under the bracts. The inflorescence is therefore clean with little or no petal residue on the bract, and does not look "flowered-out" with age.

5. Miniature growth habit.

Guzmania 487-1 has not been tested under all available environmental conditions and the phenotype may vary with variations in environmental conditions such as temperature, light intensity, daylength and humidity, without, however, any variance in genotype.

The accompanying color photographic drawings show typical characteristics of 487-1, with colors being as true as possible with illustrations of this type.

The photo on Sheet 1 is of a 10-month-old plant of 487-1 grown from an off-shoot, and finished in a 10.2 cm pot.

The photo on Sheet 2 shows close-up detail of an inflorescence of 487-1.

The following description is taken from the plant illustrated on Sheets 1 and 2. The plant was grown in Lithia, Fla. by the inventor in greenhouse conditions which are typical of the industry. Color references are made to The Royal Horticultural Society Colour Chart.

I. Plant:

*Form.*—Basal rosette of strap-like leaves arranged around a central axis.

*Height.*—Approximately 25 cm including inflorescence.

*Diameter.*—Approximately 50–55 cm.

II. Foliage:

*Size of leaf.*—The basal leaves are approximately 31–34 cm long, and 2.1–2.4 cm wide (flattened). At their widest point near the base, the leaves are approximately 5.0–5.2 cm wide.

*Shape of leaf.*—The leaf blade is ligulate with an acute tip. The surface is channeled. The margins are entire. The leaves are held upright, and are curved outward over their length.

*Surface texture.*—The leaf blade is thin, smooth and glossy.

*Color.*—The leaves are medium green throughout the foliage. The adaxial surface is darker and greener than, but closest to, 137 A, and the abaxial surface is greener than, but closest to 147 B. The innermost leaf surfaces are flushed or striated with 187 A.

*Average number of leaves.*—The plant produces approximately 28 leaves before producing an inflorescence.

*Roots.*—Roots are white changing to brown, and wiry with fine laterals.

III. Bracts:

*Size and color.*—The uppermost terminal bracts are approximately 3.6–6.6 cm long and 0.7–1.8 cm wide; color is 43 A, with the most apical tipped with white 155 A. The primary bracts are approximately 7.2–14 cm long and 1.8–2.9 cm wide. The adaxial and abaxial surfaces are 44 A in color. The tips of the bracts are dark anthocyanous 185 A in color. The scape bracts are approximately 20–32.5 cm long, and approximately 2.5–2.8 cm wide. The adaxial surface of the scape bracts is greener than, but closest to, 137 A; the abaxial surface is greener than, but closest to, 147 B, with reddish 185 B areas where the bract separates from the scape.

*General shape.*—The bracts are ligulate with acute tips, and densely imbricate in vertical ranks along the capitate inflorescence.

*Number.*—Terminal Bracts, approximately 58. Primary Bracts, approximately 19. Scape Bracts, approximately 9.

*Texture.*—Smooth and glossy.

*Margin.*—Entire.

*Scape.*—The scape is approximately 20 cm tall, approximately 8.5–10 mm in diameter, and 145 B in color.

IV. Flowers:

*Borne.*—Terminal in the inflorescence.

*Shape of inflorescence.*—The inflorescence is star shaped when viewed from above, terminal in origin, and densely pennate.

*Individual flowers.*—Approximately 52 flowers or flower buds present, terminal in the inflorescence and concealed under bracts. Calyx: Gamosepalous, three sepals present 2.4 cm long, 155 D in color. Corolla: Gameopetalous, three petals present 4.1 cm long, yellow 2 B, with white 155 D tips.

*Time of blooming.*—In mature plants, flowering begins 10–12 weeks after induction, at any time of the year.

*Duration of inflorescence.*—The inflorescence will hold its color approximately 4–8 months. Individual flowers last 1 day, and the total duration of flowering is about 7–10 weeks.

V. Reproductive organs:

*Ovary.*—Superior, three locules, 7 mm long, 150 D in color.

*Style.*—3.2 cm long, 155 D in color.

*Stamens.*—Six present, filament 3.3 cm long, anthers 6 mm long, yellow 3 D in color.

VI Seed characteristics: Sterile F1 hybrid.

It is claimed:

1. A new and distinct cultivar of Guzmania named 487-1, as illustrated and described.

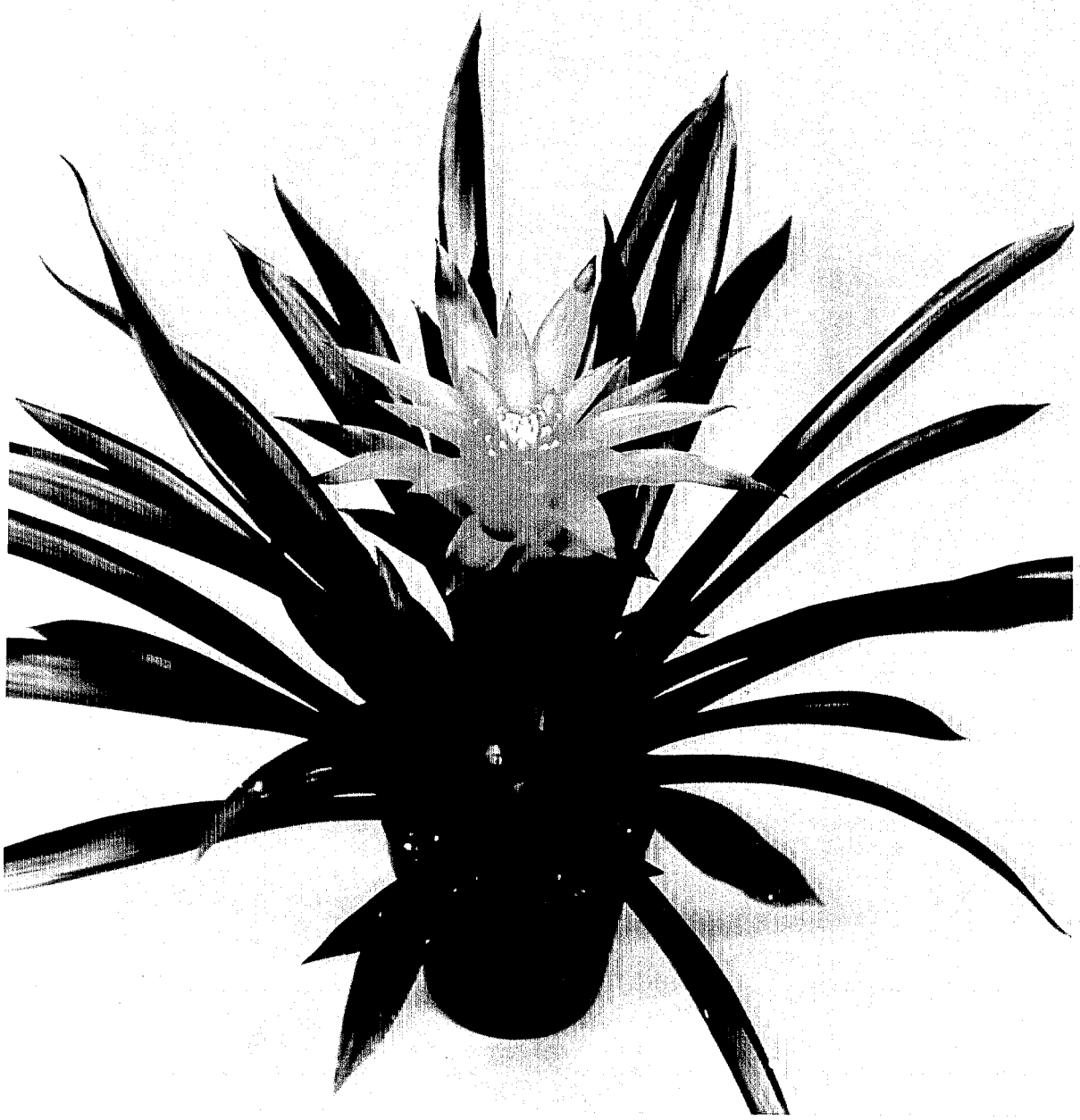

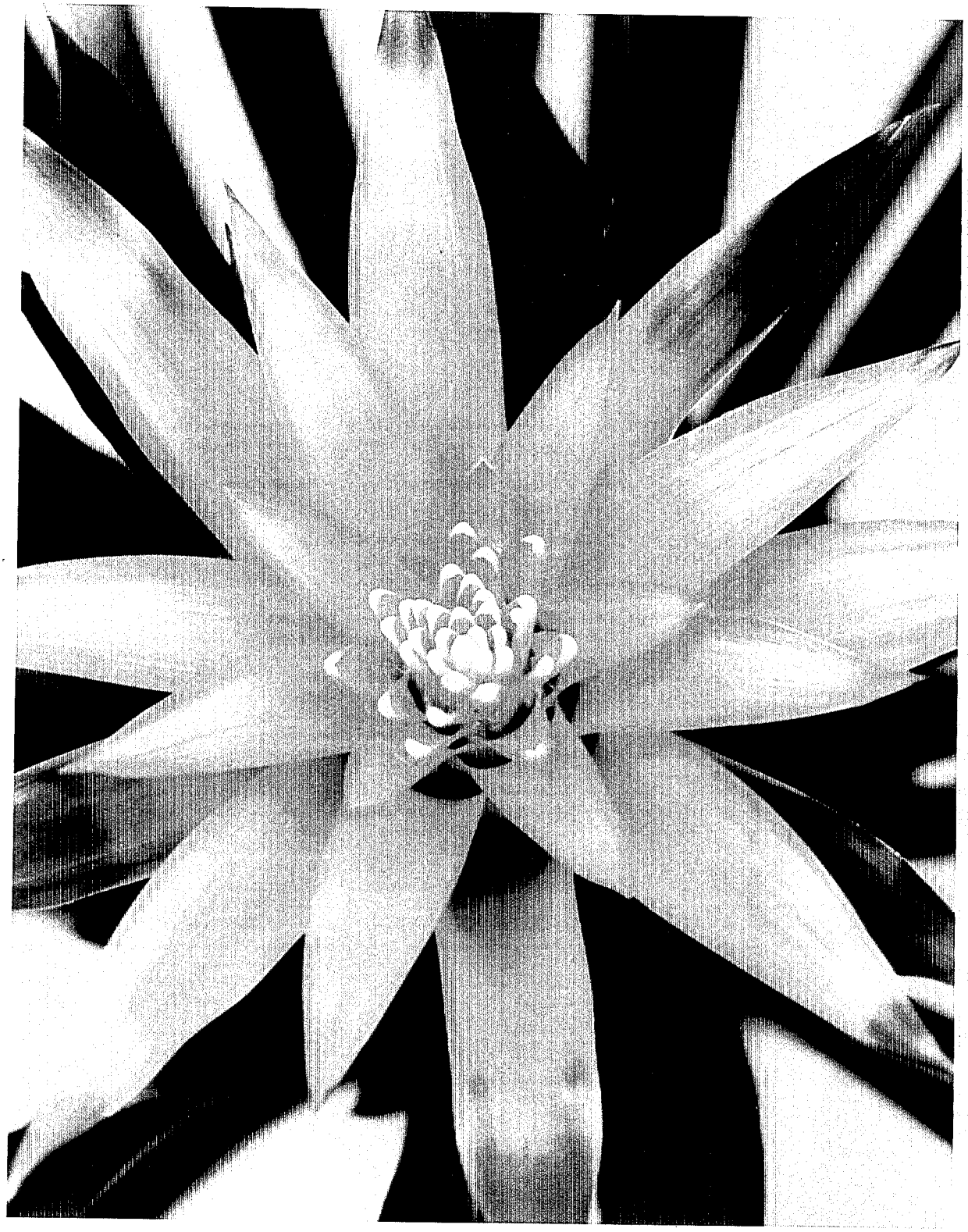

* * * * *